United States Patent [19]

Horn

[11] Patent Number: 4,475,559
[45] Date of Patent: Oct. 9, 1984

[54] APPARATUS AND METHOD FOR DETECTING APNEA

[76] Inventor: Mary Horn, 232 Aspinwall Ave., Brookline, Mass. 02146

[21] Appl. No.: 310,092

[22] Filed: Oct. 9, 1981

[51] Int. Cl.$^3$ .............................................. A61B 5/08
[52] U.S. Cl. ................................... 128/716; 128/773; 128/207.18; 215/11 R
[58] Field of Search ............... 128/716, 773, 724, 725, 128/359, 360, 207.18; 215/11 R

[56] References Cited

U.S. PATENT DOCUMENTS

| | | | |
|---|---|---|---|
| 408,938 | 8/1889 | Tata | 128/716 |
| 2,376,971 | 5/1945 | Kleit | 128/725 X |
| 2,750,938 | 6/1956 | Bier | 128/716 |
| 2,868,199 | 1/1959 | Hudson | 128/207.18 |
| 2,904,033 | 9/1959 | Shane | 128/716 |
| 3,530,850 | 9/1970 | Edwards | 128/716 |
| 3,611,801 | 10/1971 | Paine | 128/716 |
| 3,884,219 | 5/1975 | Richardson et al. | 128/724 |

OTHER PUBLICATIONS

"Baby-Spirocust", Fresenius Apparatebau KG Bad Homburg v.d. Hohe Daimerstrasse 22, West Germany.
Hiatt et al., "Continuous Monitoring of PO$_2$ During Apnea of Prematurity" The Journal of Pediatrics, Feb., 1981.
Dronsfield et al., "A Noninvasive Method for Recording Central and Obstructive Apnea with Bradycardia in Infants" Critical Care Medicine vol. 8, No. 11, Nov., 1980.
Yasunaga et al., "Evaluation of a Sensor Pad Apnea Monitor" Illinois Medical Journal, vol. 149, No. 5, May, 1976.
Lazarus, "Pulmonary Function Tests in Upper Airway Obstruction" Respiratory Care, vol. 25, No. 6, Jun., 1980.
Stark et al., "Recovery of Airway Patency After Obstruction in Normal Infants" American Review of Respiratory Disease, vol. 123, 691–693, 1981.
Krumpe et al., "Use of Laryngeal Sound Recordings to Monitor Apnea" American Review of Respiratory Disease, vol. 122, 1980.
Duffty et al., "Respiratory Induction Plethysmography (Respitrace TM) An Evaluation of its Use in the Infant[1,2]", Am. Review of Respiratory Disease, vol. 123, 542–546, 1981.
Wilson et al., "Coordination of Breathing and Swallowing in Human Infants" J. Appl. Physisiol. 50(4), 851–858, 1981.

Primary Examiner—Kyle L. Howell
Assistant Examiner—John C. Hanley
Attorney, Agent, or Firm—Kenway & Jenney

[57] ABSTRACT

Apnea monitoring apparatus and method for detecting the cessation of airflow through the nostrils of a human being. The apparatus includes tubing having an opening in a wall thereof and one end adapted for connection in a sound-receiving manner to the human ear. The tubing is supported around the periphery of the top of a feeding bottle near the nipple so that the opening in the tubing is within the airflow. With this arrangement breathing sounds can be clearly heard so that the cessation of breathing is evident.

7 Claims, 7 Drawing Figures

APPARATUS AND METHOD FOR DETECTING APNEA

BACKGROUND OF THE INVENTION

This invention relates to apparatus and method for detecting apnea, and more particularly to apparatus capable of detecting the cessation of airflow through the nostrils of a human infant.

Apnea is defined as the cessation of airflow generally for a period exceeding ten seconds. Apnea which lasts for a sufficient period can result in brain damage or even death. Apnea is believed to contribute in some instances to sudden infant death syndrome or so-called crib death. Because apnea is a life threatening condition, it is highly desirable to monitor those believed susceptible to apnea so that if breathing does cease steps can be taken to revive the affected individual. Infants suffering from respiratory distress syndrome or other diseases are particularly susceptible to the onset of apnea. Apnea in such infants may sometimes occur during bottle feeding.

Because of the potentially extreme seriousness of the condition, many apnea monitors have been developed to warn of the onset of the condition. Heretofore, several different parameters have been monitored to infer the onset of apnea. For example, chest or abdominal wall motion can be detected using strain gauge transducers or inductive plethysmographic coils. The onset of apnea is inferred if the chest wall or abdominal wall cease moving. Other techniques monitor the change in volume of the thoracic cavity or pressure changes within the lungs. Another indirect technique is the chemical analysis of the respiratory gases.

A more direct way of detecting obstructive apnea onset is to monitor airflow through the nostrils. The direct measurement of obstructive apnea by observing airflow is often a superior technique to impedance monitoring because in certain situations the other measurements can give false indications of obstructive apnea. For example, if chest and abdominal wall motions are monitored, it is possible for apnea to go undetected if there is an obstruction in the airway passages, for, in this case, the chest wall may still move without air flowing through the nostrils and into and out of the lungs. It will however pick up nonobstructive central apnea.

Several techniques are known for directly observing the onset of apnea by detecting airflow through the nostrils. These techniques include placing a mask over the subject's face and detecting apnea by means of a pneumotachygraph. Another technique is to place a thermistor in the airflow. In this case cessation of airflow will disrupt the normal temperature dependent changes in the resistance of the thermistor, allowing apnea to be detected. The known methods for monitoring the onset of apnea directly, that is, by monitoring airflow, are technically sophisticated and expensive to make and use which limits their universal applicability. The known apnea monitors also are not well suited for detecting apnea during the feeding of an infant. Clearly, a face mask would preclude feeding, and the placing of a thermistor near the nostrils of an infant might similarly disrupt attempts at feeding by annoyance to the infant and would also require electronic equipment to monitor resistance changes in the thermistor. Since it is known that apnea can occur during feeding, it is thus important to have an apnea monitor which is particularly well adapted for use during the feeding of infants.

It is therefore an object of this invention to provide apparatus and method for detecting apnea directly, that is, by detecting the cessation of airflow, in a simple, very inexpensive, easy to operate manner.

It is a further object of this invention to provide such an apnea monitor which is effective during the feeding of an infant.

Yet another object of this invention is an apnea monitor which is very sensitive and accurate.

A still further object is an apnea monitor capable of delivering oxygen or aerosol at feeding.

Other objects, features and advantages of this invention will be pointed out hereinafter.

SUMMARY OF THE INVENTION

The apnea detecting apparatus for detecting the cessation of airflow through the nostrils of a human infant according to the present invention includes tubing having an opening in a wall thereof and one end adapted for connection to sound monitoring apparatus. Structure is provided for supporting the opening in the tubing so as to intercept the airflow exiting from the nostril. In this way, the absence of sound detected by the sound-monitoring apparatus indicates the onset of apnea. In a preferred embodiment the sound monitoring apparatus is simply the human ear. Alternatively, a microphone may be connected to the tubing for monitoring the airflow sounds.

In one embodiment of the invention the tubing is supported near the nipple of a feeding bottle so that the opening in the tube intercepts the flow through the nostrils. Alternatively, the tubing may be affixed to a baby pacifier so that the opening in the tube receives the flow through the nostrils.

In yet another embodiment the tube includes a port for receiving oxygen and delivering it through the opening in the tube to the vicinity of the nostrils of the person being monitored. This port is preferably a second opening in the tube and sliding apparatus is provided for closing this opening when oxygen is not being administered. Alternatively, the port may include a flap for closing the second opening in the tube.

BRIEF DESCRIPTION OF THE DRAWING

The invention disclosed herein will be better understood with reference to the following drawing of which.

DESCRIPTION OF THE PREFERRED EMBODIMENTS

Figure 1:
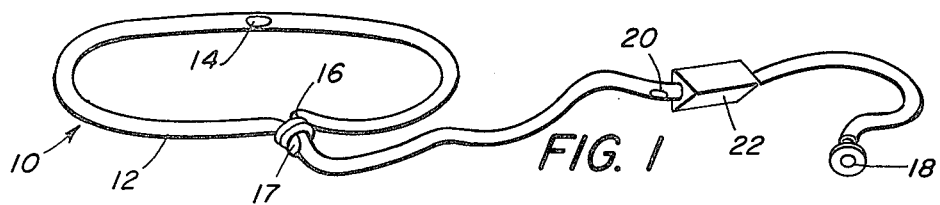
FIG. 1 is a perspective view of the apnea monitor disclosed herein.

With reference first to FIG. 1, the apnea detecting device disclosed herein is represented generally at 10.

Figure 2:
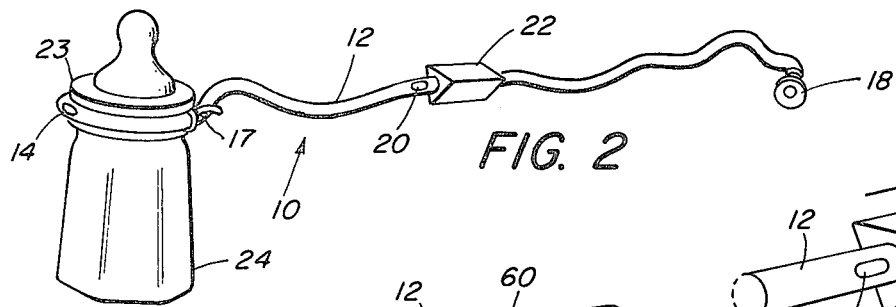
FIG. 2 is a perspective view showing the apnea monitor installed on a feeding bottle.

The detector 10 includes a length of tubing 12 which preferably is so-called "green" tubing having a diameter of about ⅜ inch used in surgical settings for delivering oxygen to a human patient. Such standard tubing is readily available from medical supply houses. As shown in FIG. 1, the tubing is looped to form a substantially circular portion at one end. The size of the loop is selected so that the looped portion will fit snugly around the top of a feeding bottle. Located within this looped portion is an opening 14 which extends through the tube 12 wall to its interior. The opening 14 is approximately 3/16 inch in diameter. The loop is maintained by means of a band 16 which along with a removable plug 17 serves to close off one end of the tube although it is not necessary that this end be tied for proper functioning. In this embodiment the other end of the tube is terminated in an earpiece 18 which is adapted for fitting within the outer portion of the human ear. Also included in the tubing 12 is a port 20 through which oxygen or an aerosol may be supplied when appropriate or breath sounds heard when the bottle is not in the mouth. The port 20 is closed by means of a sliding element 22, the operation of which will be discussed in more detail in conjunction with FIGS. 6 and 7. FIG. 2 illustrates the detecting apparatus 10 installed on a cap 23 portion of a feeding bottle 24.

Figure 4:
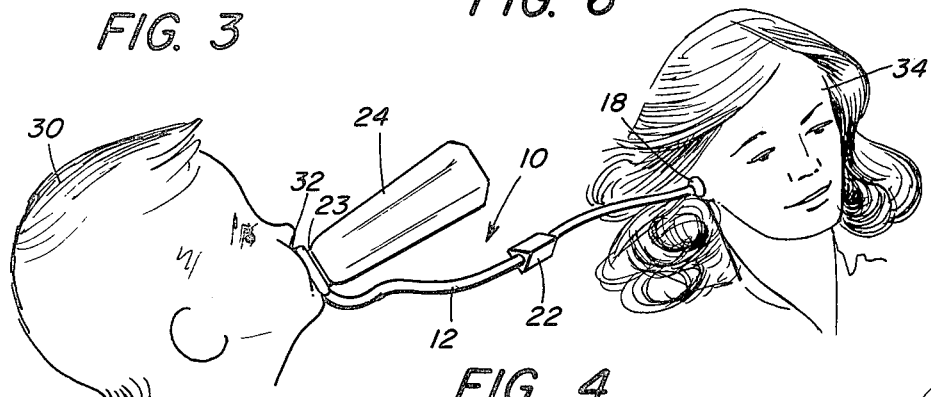
FIG. 4 is a perspective diagramatic view showing the apnea monitor in use.
Figure 5:
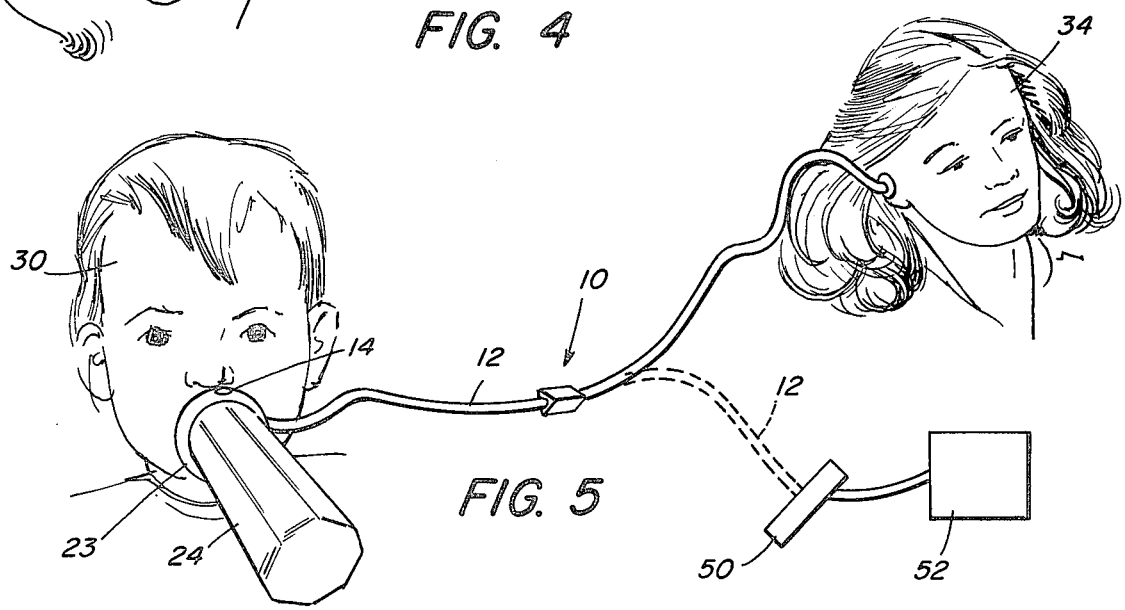
FIG. 5 is another perspective view illustrating the use of the present invention.

The operation of the apnea detector disclosed herein will now be discussed with reference to FIGS. 4 and 5. As shown in these figures, the apnea monitor or detector 10 is installed around the cap portion 23 of a feeding bottle 24 near the nipple. The bottle is placed into the mouth of an infant 30 so that the opening 14 is just below the nostrils 32. The far end of the tube 12, which terminates in the earpiece 18, is shown inserted in the ear of a person 34 responsible for detecting the onset of apnea. As the baby 30 breathes, the airflow impinges upon the opening 14, setting up sound waves in the tubing 12. The sound created by the breathing of the baby 30 can be very clearly heard through the earpiece 18 and water vapor visualized. At the onset of obstructive apnea airflow through the nostrils 32 will cease, and the absence of breathing sounds can be very clearly detected through the earpiece 18, thus indicating the onset of apnea. As shown in phantom in FIG. 5, the tube 12 may be connected to a microphone 50 whose output is connected to an electronic monitor 52. Both the microphone 50 and monitor 52 are conventionally known electronic components. The monitor 52 is adapted to produce an output signal such as an alarm when it receives no signals from the microphone 50 for an extended period such as ten seconds, indicating a cessation of breathing. It is to be noted that the feeding bottle 24 illustrated in the figures may just as well represent a pacifier which the infant 30 keeps in his mouth during periods between feedings.

Figures 3, 6, 7:
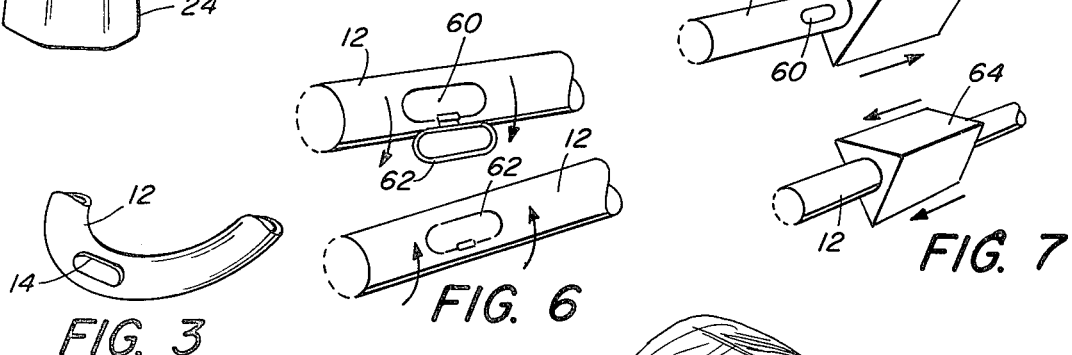
FIG. 3 is an enlarged section of the monitoring tube shown in FIG. 2.
FIG. 6 is a perspective view illustrating a port for receiving oxygen or for listening to breath sounds.
FIG. 7 is a perspective view of another means of closing an auxiliary port.

Another aspect of this invention will now be discussed with reference to FIGS. 6 and 7. Oftentimes after apnea has been detected and the proper actions have been taken to start the infant breathing again, it is desirable to administer oxygen. The apparatus disclosed herein allows oxygen to be supplied to the infant while he continues to be fed. To accommodate the administering of oxygen, a second port or opening 60 is provided in the tube 12. A source of oxygen at a designated percent is connected to the port 60, and this oxygen then flows through the tube and to the opening 14 in the vicinity of the infant's nostrils. When oxygen is not being administered, that is, when the apparatus is used for apnea detecting, the port 60 must be closed off. As shown in FIG. 6, the closing may be accomplished by means of a flap 62, which is adapted to close fully the port 60. Alternatively, the port 60 can be closed off by means of a sliding closure 64, which is adapted to fit in a sliding fashion over the tube 12. As shown in the upper portion of FIG. 7, the closure 64 is out of the way of the port 60, and in the lower portion of FIG. 7, the closure 64 has covered the port 60.

It is thus seen that the objects of this invention have been accomplished in that there has been disclosed a novel apnea monitor which is simple to use, easy to construct from readily obtainable components and which is highly sensitive and accurate. This detector also has the capability of administering oxygen after an apnea episode if desired. While this invention has been described with respect to its preferred embodiment, it should be understood that modifications and variations will occur to those skilled in the art, and all such modifications and variations are intended to fall within the scope of the appended claims.

What is claimed is:

1. Apnea detecting apparatus for detecting the cessation of airflow through the nostrils of a human being comprising:

tubing having an opening in a wall thereof and one end adapted for connection in a sound receiving manner to a human ear, and means for supporting said opening in said tubing within said airflow, said supporting means comprising a feeding bottle having a nipple and said tubing is supported by said bottle near said nipple.

2. Apnea detecting apparatus of claim 1 wherein said tubing further includes port means comprising a second opening in said tubing and sliding means for closing said second opening.

3. Apnea detecting method for detecting the cessation of airflow through the nostrils of a human being comprising the steps of:

attaching a tube with a hole in a wall thereof to a feeding bottle;

inserting said feeding bottle into the mouth of said human being such that said hole is located to be impinged by nasal emissions;

detecting sounds due to said nasal emissions at the end of the tube; and determining apnea from the cessation of said sounds.

4. The method of claim 3 wherein said sounds are detected with a microphone.

5. The method of claim 3 wherein said tube further includes port means for delivering oxygen through said hole.

6. The method of claim 5 wherein said port means includes a second hole in said tube and sliding means for closing said second hole.

7. The method of claim 5 wherein said port means includes a second hole in said tube and flap means for closing said second hole.

* * * * *